United States Patent [19]

Hunter et al.

[11] Patent Number: 5,423,226

[45] Date of Patent: Jun. 13, 1995

[54] FLOW MEASUREMENT SYSTEM

[75] Inventors: Robert M. Hunter; Frank M. Stewart, both of Bozeman, Mont.

[73] Assignee: Yellowstone Environmental Science, Inc., Bozeman, Mont.

[21] Appl. No.: 164,146

[22] Filed: Dec. 9, 1993

Related U.S. Application Data

[63] Continuation-in-part of Ser. No. 153,178, Nov. 16, 1993, Pat. No. 5,406,828.

[51] Int. Cl.⁶ .............................................. G01F 1/44
[52] U.S. Cl. .................... 73/861.63; 73/215
[58] Field of Search ........... 73/861.61, 861.52, 861.38, 73/861.47, 215

[56] References Cited

U.S. PATENT DOCUMENTS

| | | |
|---|---|---|
| 2,577,548 | 12/1951 | Vetter . |
| 2,604,778 | 7/1952 | Marquardt . |
| 2,668,438 | 2/1954 | Marquardt . |
| 2,755,669 | 7/1956 | Beard . |
| 3,380,463 | 4/1968 | Trethewey . |
| 3,399,573 | 9/1968 | Ponsar . |
| 3,460,394 | 8/1969 | Cryer . |
| 3,613,456 | 10/1971 | Hoppe et al. . |
| 3,620,085 | 11/1971 | Khoi . |
| 3,924,612 | 12/1975 | Dempster et al. ............... 73/861.38 |
| 4,307,609 | 12/1981 | Rosenblum . |
| 4,338,827 | 6/1983 | Palmer et al. . |
| 4,367,652 | 1/1983 | Venuso . |
| 4,393,705 | 7/1983 | Eidshun . |
| 4,419,893 | 12/1983 | Baillie et al. . |
| 4,476,707 | 10/1984 | Burns et al. ...................... 73/861.52 |
| 4,485,675 | 12/1984 | Verret . |
| 4,526,035 | 7/1985 | Auchapt et al. . |
| 4,571,997 | 2/1986 | Kepple et al. . |
| 4,625,548 | 12/1986 | Charter . |
| 4,669,308 | 6/1987 | Jorritsma . |
| 4,711,127 | 12/1987 | Hafner . |
| 4,719,799 | 1/1988 | Wicks et al. . |
| 4,799,388 | 1/1989 | Hunter . |
| 4,869,104 | 9/1989 | Saito et al. . |
| 4,879,912 | 11/1989 | Suckow ............................ 73/861.61 |
| 4,896,542 | 1/1990 | Hunter . |
| 4,949,572 | 8/1990 | Wilen et al. . |
| 5,020,368 | 6/1991 | Evans et al. . |
| 5,052,222 | 10/1991 | Stoepfel . |
| 5,199,306 | 4/1993 | Hunter . |

OTHER PUBLICATIONS

Dedrick & Clemens, Double–Bubblers Coupled with Pressure Tranducers for Water Level Sensing, Trans. ASAE, 779–783, 1984.

Dedrick & Clemmens, Instrumentation for Monitoring Water Levels, Proceedings of the Agri–Mation 2 Conference & Exposition, Mar. 3–5, Chicago, Ill., p. 148, 1986.

*Primary Examiner*—Richard E. Chilcot, Jr.
*Assistant Examiner*—Harshad Patel

[57] ABSTRACT

A portable flow measurement system comprising a primary flow metering element and a secondary flow metering element is disclosed that will find application in metering irrigation water use, urban and rural storm water runoff, infiltration/inflow and wastewater flow rates. The primary element comprises a constriction in a closed conduit that produces pressures in the liquid flowing through it that are related to the rate of flow of the liquid. The constriction is preferably configured to cause essentially simultaneous filling of the constriction and the conduit upstream from it upon increasing flow rate and/or filling of the constriction and/or the upstream pipe before the modular limit is reached. The secondary element comprises a system for transmitting and sensing the pressures produced by the primary element, computing flow rates using the sensed pressure as a basis and storing the pressure data and/or the flow rate data. The pressure transmitting and sensing subassembly comprises a plurality of bubbler circuits, a plurality of mechanisms for controlling bubble release rate, at least one and preferable two differential pressure sensors, mechanisms for simultaneously applying the same pressure to the pressure side and the reference side of each differential pressure sensor and mechanisms for simultaneously applying a known differential pressure across each differential pressure sensor.

27 Claims, 5 Drawing Sheets

FLOW MEASUREMENT SYSTEM

STATEMENT AS TO RIGHTS IN INVENTIONS MADE UNDER FEDERALLY-SPONSORED RESEARCH AND DEVELOPMENT

This invention was made with Government support under Grant No. 92-33610-7212 awarded by the U.S. Department of Agriculture. The Government has certain rights in the invention.

This is a continuation in part of application Ser. No. 08/153,178, filed Nov. 16, 1993 now U.S. Pat. No. 5,406,828.

CROSS-REFERENCES TO RELATED APPLICATIONS

The invention disclosed herein provides improvements to the inventions disclosed in U.S. Pat. No. 4,799,388 by Hunter, Jan. 24, 1989, entitled "Apparatus and Technique for Metering Liquid Flow"; U.S. Pat. No. 4,896,542 by Hunter, Jan. 30, 1990, entitled "Portable Wastewater Flow Meter" and U.S. Pat. No. 5,199,306 by Hunter, Apr. 6, 1993, entitled "Method and Apparatus for Metering Flow in Closed Conduits that Surcharge." The disclosure of the aforementioned U.S. patents are incorporated by reference herein as if fully set forth.

BACKGROUND OF THE INVENTION

The background of the invention is set forth in two parts: the field of the invention and the description of related art.

Field of the Invention

This invention relates to flow rate measurement in closed conduits that surcharge. In particular, it relates to temporary flow metering in pipelines that flow full part of the time and less than full part of the time.

Description of Related Art

The background art includes that disclosed in the aforementioned U.S. patents. Those references disclose a variety of primary flow elements and secondary flow elements. In some disclosed embodiments, the primary flow elements comprise constrictions configured to cause simultaneous filling of the constriction and the upstream pipe upon increasing flow rate. In other disclosed embodiments, the primary flow elements comprise constrictions configured to cause filling of the constriction and/or the upstream pipe before the modular limit of the device is reached. The disclosed secondary flow elements utilize a variety of means to transmit and sense the level and pressure changes caused by the primary flow elements. One such means comprises a bubbler-type pressure transmitting and sensing system.

A variety of bubbler-type pressure transmitting and sensing systems have been disclosed in prior art references. Bubbler-type systems for level sensing are disclosed in U.S. Pat. Nos. 3,620,085 by Khoi, Nov. 16, 1971; 4,526,035 by Auchapt et al., Jul. 2, 1985; 4,625,548 by Charter, Dec. 2, 1986; 4,711,127 by Hafner, Dec. 8, 1987; 4,719,799 by Wicks et al., Jan. 19, 1988; 4,869,104 by Saito et al., Sep. 26, 1989 and 5,052,222 by Stoepfel, Oct. 1, 1991. Bubbler-type systems for density sensing are disclosed in U.S. Pat. Nos. 2,557,548 by Vetter, Dec. 4, 1951; 2,604,778 by Marquardt, Jul. 29, 1952; 2,668,438 by Marquardt, Feb. 9, 1954; 2,755,669 by Beard, Jul. 24, 1956; 3,380,463 by Trethewey, Apr. 30, 1968; 3,399,573 by Ponsar, Sep. 3, 1968; 3,460,394 by Cryer, Aug. 12, 1969; 3,613,456 by Hoppe et al., Oct. 19, 1971; 4,307,609 by Rosenblum, Dec. 29, 1981; 4,393,705 by Eidshun, Jul. 19, 1983; 4,419,893 by Baillie et al., Dec. 13, 1983; 4,485,675 by Verret, Dec. 4, 1984; 4,949,572 by Wilen et al., Aug. 21, 1990 and 5,020,368 by Evans et al., Oct. 1, 1991. Bubbler-type systems for flow metering are disclosed in U.S. Pat. Nos. 4,367,652 by Venuso, Jan. 11, 1983; 4,388,827 by Palmer et al., Jun. 21, 1983 and 4,669,308 by Jorritsma, Jun. 2, 1987.

Bubbler-type pressure transmitting and sensing systems are also disclosed by A. R. Dedrick and A. J. Clemmens in "Double-Bubblers Coupled with Pressure Transducers for Water Level Sensing" in *Transactions of the ASAE*, 1984, p. 779, and A. R. Dedrick and A. J. Clemmens in "Instrumentation for Monitoring Water Levels" in *Proceedings of the Agri-Mation TM 2 Conference & Exposition*, Mar. 3–5, 1986, Chicago, Ill., p. 148. These systems implement the "double bubbler" concept in which the pressure in two bubbler tubes is determined sequentially by means of a gauge pressure sensor referenced to atmospheric pressure. The ends of the bubbler tubes are submerged in water and are located a known vertical distance apart in fresh water. The known head differential is used to calibrate the gain of the pressure sensor. In that the gauge pressure sensor can be zeroed by venting its pressure port to atmospheric pressure, both the offset and span of the sensor can be recalibrated prior to use of the pressure sensor to measure the unknown pressure in one of the bubbler tubes. Limitations of this system include the sequential exposure of a gauge pressure sensor to the pressures in two different bubbler circuits to reset gain and incorporation of bulky and heavy needle valves and differential pressure regulators into the system.

SUMMARY OF THE INVENTION

The present invention provides an improved flow measurement system which may be portable or permanently installed. The system is comprised of two elements: a primary element and a secondary element. The primary element comprises a constriction in a closed conduit that produces pressures in liquid flowing through it that are related to the rate of flow of the liquid. In one embodiment, the constriction is configured by reference to the patents noted above to cause essentially simultaneous filling of the constriction and the conduit upstream from it upon increasing flow rate. In other disclosed embodiments, the primary flow elements comprise constrictions configured to cause filling of the constriction and/or the upstream pipe before the modular limit of the device is reached. For the purposes of this disclosure, the term "modular limit" means the point at which an increase in the water level downstream from a constriction (tail water depth) begins to affect the water level upstream from the constriction.

The primary element (constriction) can be installed in a pipe of any size or shape. The throat can be almost any shape, but the top of the throat is preferably flat. Design of the constriction involves selection of a conventional critical depth flume design and then adding a top sill. The elevation of the bottom surface of the top sill may be chosen to effectively lower the top of the throat so that the throat fills with liquid at the same flow rate as the upstream pipe fills with liquid on increasing flow rate. Alternatively, the elevation of the bottom surface of the top sill may be chosen so as to cause either the throat or the upstream pipe to fill first on increasing flow rate.

Either hydraulic theory or laboratory calibration can be used to develop discharge equations for such primary elements. A theoretical open channel calibration curve can be based on simultaneous solution of the following equations:

$$Q=[2g(Y_1-Y_2-z)]^{\frac{1}{2}}*A_1/[(A_1/A_2)^2-1]^{\frac{1}{2}}$$

$$Q=[(A_2^3/T_2)*g]^{\frac{1}{2}}$$

where
 Q=flow rate
 g=acceleration due to gravity
 $Y_1$=inlet section depth of flow
 $Y_2$=depth of flow in throat section
 z=throat sill height
 $A_1$=inlet area of flow
 $A_2$=area of flow in throat
 $T_2$=top width of flow in throat In that simultaneous solution of the above equations can be used to predict the elevation of the top of the water surface in the inlet section (section 1) when the elevation of the top of the water surface in the throat section (section 2) is known (or assumed) and visa versa. These equations can be used to design the design to cause simultaneous or sequential filling of the throat and inlet (e.g., upstream pipe) sections. Given the modular limit (maximum submergence) of a particular meter design (which can vary between 60 and 95 percent), the above equations can also be used to size the throat section relative to the upstream section to cause simultaneous or sequential filling of the throat and upstream closed conduit before the modular limit is reached.

Under full-pipe conditions (above the open channel capacity of the flow tube) a calibration curve may be obtained from the following discharge equation:

$$Q=[2g(h_1-h_2)]^{\frac{1}{2}}*A_1/A_2)^2-1]^{\frac{1}{2}}$$

where
 $h_1-h_2$=difference in pressure head between the inlet and throat sections.
 Q=flow rate
 g=acceleration due to gravity
 $A_1$=inlet area of flow
 $A_2$=area of flow in throat The secondary element comprises a system for transmitting and sensing the pressures produced by the primary element, means for computing flow rates using the sensed pressure as a basis and means for transmitting and storing the pressure data and/or the flow rate data. The pressure transmitting and sensing system comprises a plurality of bubbler circuits, a plurality of means for controlling bubble release rate, at least one and preferably two differential pressure sensors, means for simultaneously applying the same pressure to the pressure side and the reference side of each differential pressure sensor and means for simultaneously applying a known differential pressure across each differential pressure sensor. In some embodiments, the system includes a datalogger/controller, an interface circuit board, and a computer. In other embodiments, flow and other data are transmitted from the datalogger/controller to a computer over telephone lines via a modem. In yet other embodiments, flow and other data are transmitted from the datalogger/controller to a computer by means of a conventional packet radio station.

The present invention provides a variety of advantages over the prior art. One object of the invention is to essentially eliminate the effect of pressure sensor temperature variations on flow meter accuracy. Another object of the invention is to essentially eliminate the effect of long-term pressure sensor drift on flow meter accuracy. Another object of the invention is to provide meter users with another choice of pressure transmitting and sensing techniques. This is important to users who, for whatever reason, prefer the bubbler technique to the submersible pressure transducer technique for pressure transmission and sensing.

The present invention has advantages in situations wherein the measured pressure is rapidly varying in that simultaneous pressure differential measurements are used to recalibrate pressure sensor span. It also provides a compact and lightweight method for recalibration of relatively inexpensive pressure sensors. Further objects and advantages of the invention will become apparent from consideration of the drawings and the ensuing description of it.

BRIEF DESCRIPTION OF THE DRAWINGS

The features of the invention will be better understood by reference to the accompanying drawings which illustrate presently preferred embodiments of the invention.

In the drawings.

The following reference numerals are used to indicate the parts of the invention on the drawings:
1 apparatus for pressure and level transmission and sensing
2 compressor, air pump, or source of compressed gas
3 portable flow measurement system
4 first balancing orifice
6 second balancing orifice
8 third balancing orifice
10 first solenoid valve
12 second solenoid valve
14 third solenoid valve
16 first adjustable spring-biased comparitor
18 second adjustable spring-biased comparitor
20 third adjustable spring-biased comparitor
22 fourth orifice
24 fifth orifice
26 sixth orifice
28 seventh orifice
40 fourth solenoid valve
42 fifth solenoid valve
44 sixth solenoid valve
46 first bubbler port, first bubble-releasing port or first means for releasing bubbles
48 second bubbler port, second bubble-releasing port or second means for releasing bubbles
50 third bubbler port, third bubble-releasing port
52 first bubbler circuit
54 second bubbler circuit 56 third bubbler circuit
60 seventh solenoid valve
62 first differential pressure sensor
64 eighth solenoid valve
66 second differential pressure sensor
70 atmosphere
72 gauge pressure sensor or transducer
80 ninth solenoid valve
84 U-tube manometer
90 pneumatic integrated circuit
92 manifold
102 primary flow metering element or primary element
104 constriction
106 closed conduit or pipeline
110 computer means or computer
154 throat
156 inlet
158 outlet
160 secondary flow metering element or secondary element
164 datalogger/controller
170 first bubble regulator or first bubble rate controller
172 second bubble regulator or second bubble rate controller
174 third bubble regulator or third bubble rate controller
180 calibration pressure source
182 air filter
202 plurality of bubbles
210 first layer
212 second layer
214 third layer
282 remote communications interface

DESCRIPTION OF THE PREFERRED EMBODIMENTS

Figure 1:
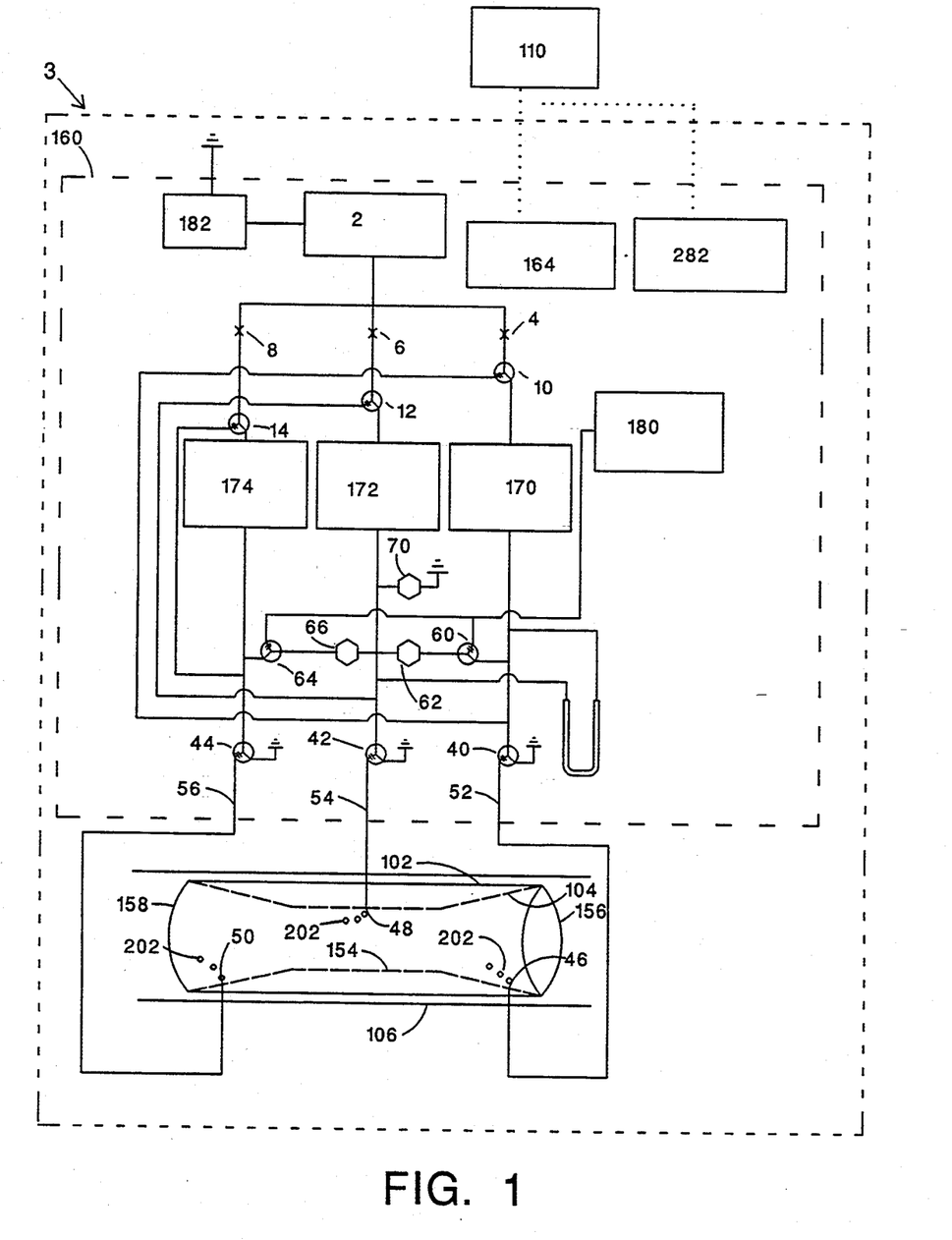
FIG. 1 is a highly schematic block diagram of the portable flow measurement system.

Reference is now made to FIG. 1 which is a highly schematic block diagram of a representative embodiment of portable flow measurement system 3. The system is comprised of two elements: primary flow metering element 102 and secondary flow metering element 160. Primary element 102 comprises constriction 104 in closed conduit 106 that produces pressures in the liquid flowing through it that are related to the rate of flow of the liquid. In preferred embodiments, constriction 104 is configured by reference to the patents noted above to cause essentially simultaneous filling of throat 154 of constriction 104 and the closed conduit upstream from it upon increasing flow rate. Also in preferred embodiments, constriction 104 is configured to cause filling of constriction 104 before the modular limit of primary element 102 is reached. Primary element 102 also comprises first bubble-releasing port 46 in inlet 156 of primary element 102, second bubble-releasing port 48 in throat 154 of primary element 102 and third bubble-releasing port 50 in outlet 158 of primary element 102.

Secondary element 160 comprises an apparatus for pressure and level transmitting and sensing, said pressures being produced by primary element 102. Secondary element 160 also comprises means for computing flow rates using the sensed pressures as a basis and means for storing the pressure data and/or the flow rate data. In a preferred embodiment, the means for computing and the means for storing is datalogger/controller 164.

Air is drawn into secondary element 160 through air filter 182 by compressor 2. Air filter 182 is preferably a hydrophobic filter that will remove water droplets as well as solid particulates from the air. The components of secondary element 160 are battery operated and compressor 2 operates only when pressure measurement is required in order to conserve energy, and, hence, battery life.

Secondary element 160 contains a plurality of bubbler circuits. First bubbler circuit 52 is connected to and discharges a plurality of bubbles 202 through first bubble-releasing port 46 in primary element 102. Second bubbler circuit 54 is connected to and discharges a plurality of bubbles 202 through second bubble-releasing port 48 in primary element 102. Third bubbler circuit 56 is connected to and discharges a plurality of bubbles 202 through third bubble-releasing port 50 in primary element 102.

In preferred embodiments, secondary element 160 also comprises a plurality of means for controlling bubble release rate. First bubble regulator or first bubble rate controller 170 controls the gas flow rate in first bubbler circuit 52. Second bubble regulator or second bubble rate controller 172 controls the gas flow rate in second bubbler circuit 54. Third bubble regulator or third bubble rate controller 174 controls the gas flow rate in third bubbler circuit 56. In alternative embodiments, only two bubbler circuits and two bubble rate controllers are provided within the secondary element and circuitry and valving are provided to allow sensing of all three pressures.

Similarly, preferably two differential pressure sensors and one gauge sensor are provided in secondary element 160. First differential pressure sensor 62 is used to sense the differential pressure between bubbler circuits 52 and 54. Second differential pressure sensor 66 is used to sense the differential pressure between bubbler circuits 56 and 54. Gauge pressure sensor 70 is used to sense the gauge pressure in bubbler circuit 54.

Means are provided for simultaneously applying the same pressure to the pressure side and the reference side of each differential pressure sensor. Also, means are provided, such as calibration pressure source 180, for simultaneously applying a known differential pressure across each differential pressure sensor.

In a preferred embodiment, data contained in datalogger/controller 164 is communicated to computer 110 via a conventional RS-232 asynchronous communications link. Preferably, computer 110 is a portable computer, such as a lap top or note book computer.

In an alternative embodiment, secondary element 160 comprises remote communication interface 282, by means of which datalogger/controller 164 is configured (programmed) and interrogated. In one alternative embodiment, remote control interface 282 is a modem connected by a telephone line (not shown) to a modem associated with computer 110.

In another alternative embodiment, remote control interface 282 is a packet radio station or infrared transmitter/receiver. A packet radio station is capable of sending via radio a fractional-second burst of encoded data and message called a packet. A packet frame is encoded according to the American Radio Relay League (ARRL) protocol. Up to seven frames with up to 256 data bytes per frame can be sent in one packet. A receiving station (not shown) decodes the packet and sends it to a computer 110 via an RS-232 asynchronous communications link. A packet radio station is available commercially from Advanced Electronics Applications, Inc. of Lynnwood, Wash. A design for a remote control and telemetry system that incorporates a packet radio station is described by P. Newland in "Introducing METCON, a New Remote Control and Telemetry System" in *QST*, Jan., 1993, p. 41.

In alternative embodiments, satellite telemetry or infrared signals are used to establish a communications link between secondary element 160 and computer 110. Data may be transmitted to a satellite via radio signals and the satellite transmits the data to a receiving station on earth via radio signals. Over shorter distances, data may be transmitted via infrared signals.

Figure 2:
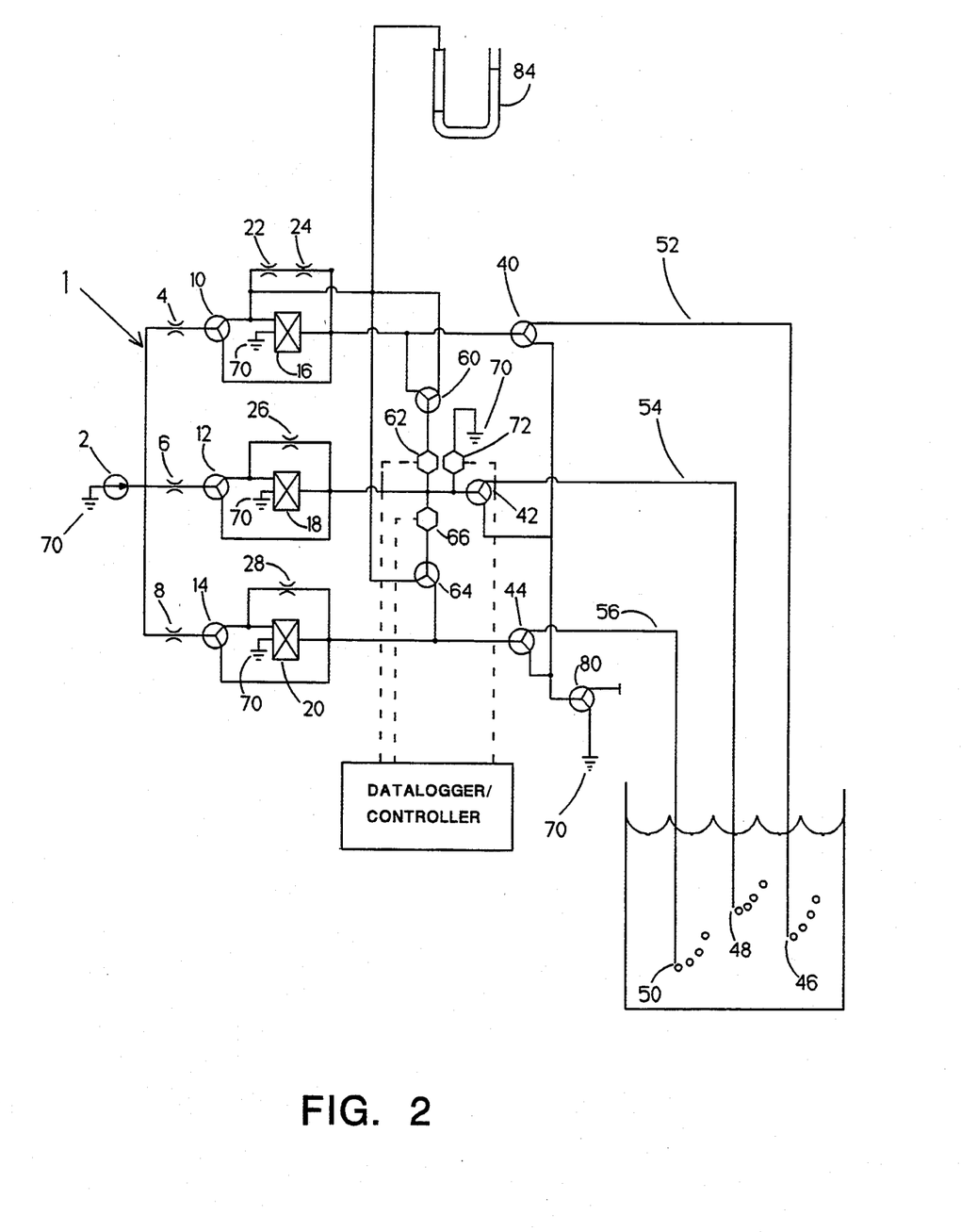
FIG. 2 is a highly schematic pneumatic diagram of the apparatus for pressure and level transmission and sensing.

Reference is now made to FIG. 2 which is a highly schematic pneumatic diagram of a representative embodiment of apparatus for pressure and level transmission and sensing 1. This embodiment is capable of measuring two differential pressures and one gauge pressure. Compressor or air pump 2 provides compressed gas by removing air from the ambient atmosphere 70 and pressurizing it.

Solenoid valves 10, 12, 14, 40, 42, 44, 60, 64, and 80 are three way valves. Said valves have an open air passage between their common port and normally open port when they are deactivated (no electrical power applied), and an open air passage between their common port and normally closed port when they are activated (electrical power applied).

During normal bubbling operations, electrical power is applied to activate compressor 2, forth solenoid valve 40, fifth solenoid valve 42, and sixth solenoid valve 44. The remaining solenoid valves 10, 12, 14, 60, 64, and 80 are deactivated. Compressed air flows in parallel through (1) first balancing orifice 4, first solenoid valve 10, first adjustable springbiased comparitor 16 and forth orifice 22 and fifth orifice 24, (2) second balancing orifice 6, second solenoid valve 12, second adjustable spring-biased comparitor 18 and sixth orifice 26, and (3) third balancing orifice 8, third solenoid valve 14, third adjustable spring-biased comparitor 20 and seventh orifice 28. Flow in parallel through each adjustable spring-biased comparitor and orifice (or orifice pair) maintains the bubble rate in each circuit relatively constant over a wide range of pressures in each circuit.

In some embodiments, a receiver (tank) pressurized to a fixed differential pressure above the pressure in one of the bubbler circuits is used to control bubble rate in all bubbler circuits. The fixed pressure differential is maintained by a compressor activated by means of a pressure switch on the tank referenced to pressure in the bubbler circuit.

Compressed air flows through activated fourth solenoid valve 40 into the portion of the first bubbler circuit 52 leading to first bubbler port 46 that discharges a plurality of bubbles 202. Similarly, air flowing through activated fifth solenoid valve 42 discharges into the portion of second bubbler circuit 54 that discharges a plurality of bubbles 202 through second bubbler port 48 and air flowing through activated sixth solenoid valve 44 discharges into the portion of third bubbler circuit 56 that discharges a plurality of bubbles 202 through third bubbler port 50. Because bubble air flow rates are very low, essentially no head loss occurs in each bubbler circuit. Moreover, the head losses can be kept essentially equal if the tubing segments used in the bubbler circuits are equal in diameter and length.

The differential pressure between first bubbler circuit 52 and second bubbler circuit 54 is transmitted to and sensed by first differential pressure sensor 62. Similarly, the differential pressure between third bubbler circuit 56 and second bubbler circuit 54 is transmitted to and sensed by second differential pressure sensor 66. The gauge pressure in second bubbler circuit 54 is transmitted to and sensed by gauge pressure sensor 72 which is referenced to the pressure in the atmosphere 70.

In an alternative embodiment (not shown), wherein the bubble discharge ports are located significant distances from the pressure sensors, different tubes can be used to convey air to discharge ports from those tubes in which pressures are sensed. In this way, the head losses associated with air movement through the bubbler circuit tubes over long distances are not added to the pressures existing at the discharge ports.

In preferred embodiments, the bubble circuits are intermittently pressurized sufficiently to cause plurality of bubbles 202 to discharge from the bubbler ports. This mode of operation, termed non-continuous operation, is appropriate for most applications and conserves battery life. During the time intervals between measurements, all of the solenoid valves (10, 2, 14, 40, 42, 44 and 80) and the compressor 2 are deactivated. Any water which is forced back through first bubbler port and into circuit 52 during the interval between measurements is blocked by deactivated fourth solenoid valve 40. Similarly, water in second bubbler circuit 54 is blocked by fifth solenoid valve 42, and water in third bubbler circuit 56 is blocked by sixth solenoid valve 44.

In preferred embodiments, datalogger/controller 164 is programmed to accomplish a slow integration mode of analog to digital conversion of pressure sensor signals. In this mode of operation, many samples of the analog signals are obtained and averaged. In alternative embodiments, datalogger/controller 164 is programmed to accomplish a fast integration mode wherein fewer samples are obtained to characterize a rapidly varying flow rate. Under conditions of rapidly varying flow rate, datalogger/controller 164 may also be programmed (1) to cause continuous operation of the bubbler system, and (2) not to reset pressure sensor zero between each pressure measurement. In this mode, flow rate determinations can be achieved at intervals of one second or less.

In an alternative embodiment (not shown), wherein the bubble discharge ports are located significant distances from the pressure sensors, different tubes can be used to convey air to discharge ports from those tubes in which pressures are sensed. In this way, the head losses associated with air movement through the bubbler circuit tubes over long distances are not added to the pressures existing at the discharge ports.

Part of the operation of the apparatus is purging to remove liquid (e.g., water) and blockages from the bubbler circuits. During the purging operation, first solenoid valve 10 is activated to allow air flow from activated compressor 2 to bypass first adjustable spring-biased comparitor 16, first orifice 22 and second orifice 24. Similarly, second solenoid valve 12 is activated to allow air flow from compressor 2 to bypass second adjustable spring-biased comparitor 18 and third orifice 26, and third solenoid valve 14 is activated to allow air flow from compressor 2 to bypass third adjustable spring-biased comparitor 20 and forth orifice 28. Ninth solenoid valve 80 is momentarily activated in order to increase air pressure in the system upstream of said solenoid valve 80 to a pressure greater than the maximum expected water pressure at bubbler ports 46, 48, and 50. Next, fourth solenoid valve 40 is activated, allowing air to flow at a relatively high rate through first bubbler circuit 52 and out first bubbler port 46, thereby purging the first bubbler circuit 52. Similarly, fifth solenoid valve 42 and sixth solenoid valve 44 are activated, allowing air to flow through second bubbler circuit 54 and third bubbler circuit 56, and out through second bubbler port 48 and third bubbler port 50. Ninth solenoid valve 80 is deactivated immediately following the activation of fourth solenoid valve 40, fifth solenoid valve 42, and sixth solenoid valve 44. After a preset time interval (on the order of 10 seconds), first solenoid valve 10, second solenoid valve 12, and third solenoid valve 14 are deactivated, which leaves all solenoid valves in their proper positions for normal bubbler operation.

Resetting of the zeros of the pressure sensors is accomplished by simultaneously exposing both sides of each pressure sensor to atmospheric pressure. This is accomplished by deactivating fourth solenoid valve 40, fifth solenoid valve 42, sixth solenoid valve 44, seventh solenoid valve 60, eighth solenoid valve 64, and ninth solenoid valve 80 and deactivating compressor 2. After the pressure in the first, second, and third bubbler circuits bleeds out through the exhaust port of first, second, and third adjustable spring-biased comparitor 16, 18, and 20, both sides of all three pressure sensors are exposed to atmospheric pressure. After the zeros are reset, the electrical signals produced by each pressure sensor are indicative of zero pressure.

In some embodiments, the gain of first differential pressure sensor 62 and second differential pressure sensor 66 are intermittently reestablished. In a preferred embodiment, this is accomplished by deactivating fifth solenoid valve 42, activating seventh solenoid valve 60, eighth solenoid valve 64, ninth solenoid valve 80, and compressor 2. This simultaneously exposes the pressure sides of both pressure sensors to the pressure upstream from first adjustable spring-biased comparitor 16 and the reference side of both pressure sensors to atmospheric pressure. This known pressure differential is used to reestablish the gain of the pressure sensors. In some embodiments, this pressure differential can be manually reset at regular intervals (e.g., weeks or months) by adjusting adjustable spring-biased comparitor 16 by reference to U-tube manometer 84.

In other embodiments, the pressure sensors are temperature compensated by means of internal circuitry. In these embodiments, intermittent automatic resetting of the zero signals of each temperature-compensated pressure sensor, 62, 66, and 72 is sufficient to maintain pressure sensing accuracy. An example of a temperature-compensated differential pressure sensor is Motorola Model MPX2052D.

In some embodiments, the head loss produced by the adjustable spring-biased comparitor or the spring-biased differential pressure regulator varies with the temperature of the apparatus. The known differential head at any temperature can be established by developing an algorithm or curve that relates head loss to apparatus temperature. An algorithm that is appropriate for use with Airtrol Model 4104-10 spring-biased comparitors to calculate a known differential head in millimeters (mm) of water is as follows:

$$KDH = SH - 0.324 * T$$

where
KDH = known differential head, mm of water
SH = differential head set across the comparitor at 0° C., mm of water
T = temperature in degrees C In other embodiments, the variation in head loss with temperature is eliminated by incorporating springs fabricated from an alloy having a constant modulus of elasticity over a wide temperature range, such as Elinvar, Iso-Elastic, Elgiloy, Ni-Span C Alloy 902, Elinvar Extra, or Precision C into the spring-biased comparitor or differential pressure regulator.

Figure 3:
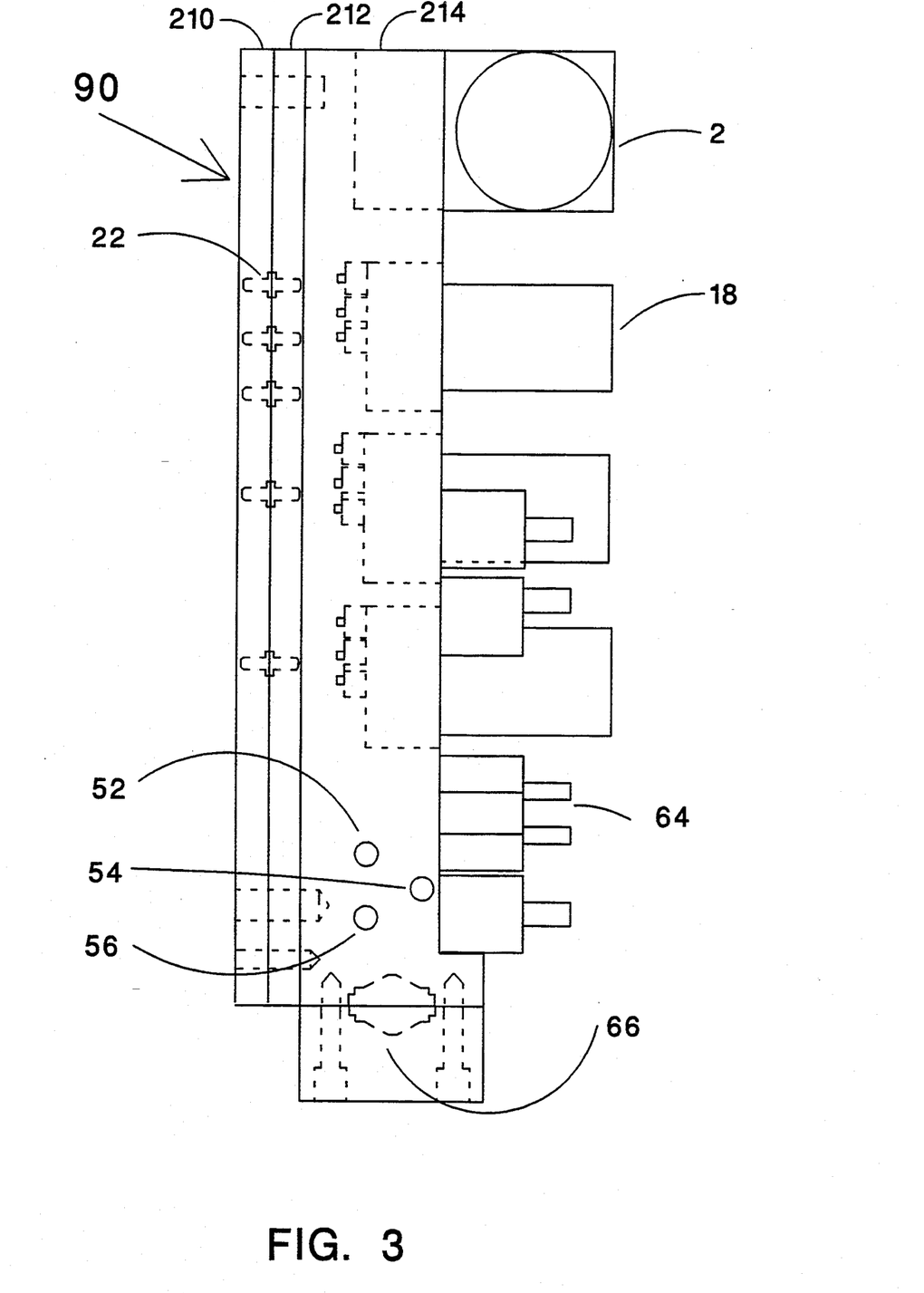
FIG. 3 is a plan view of the pneumatic integrated circuit.
Figure 4:
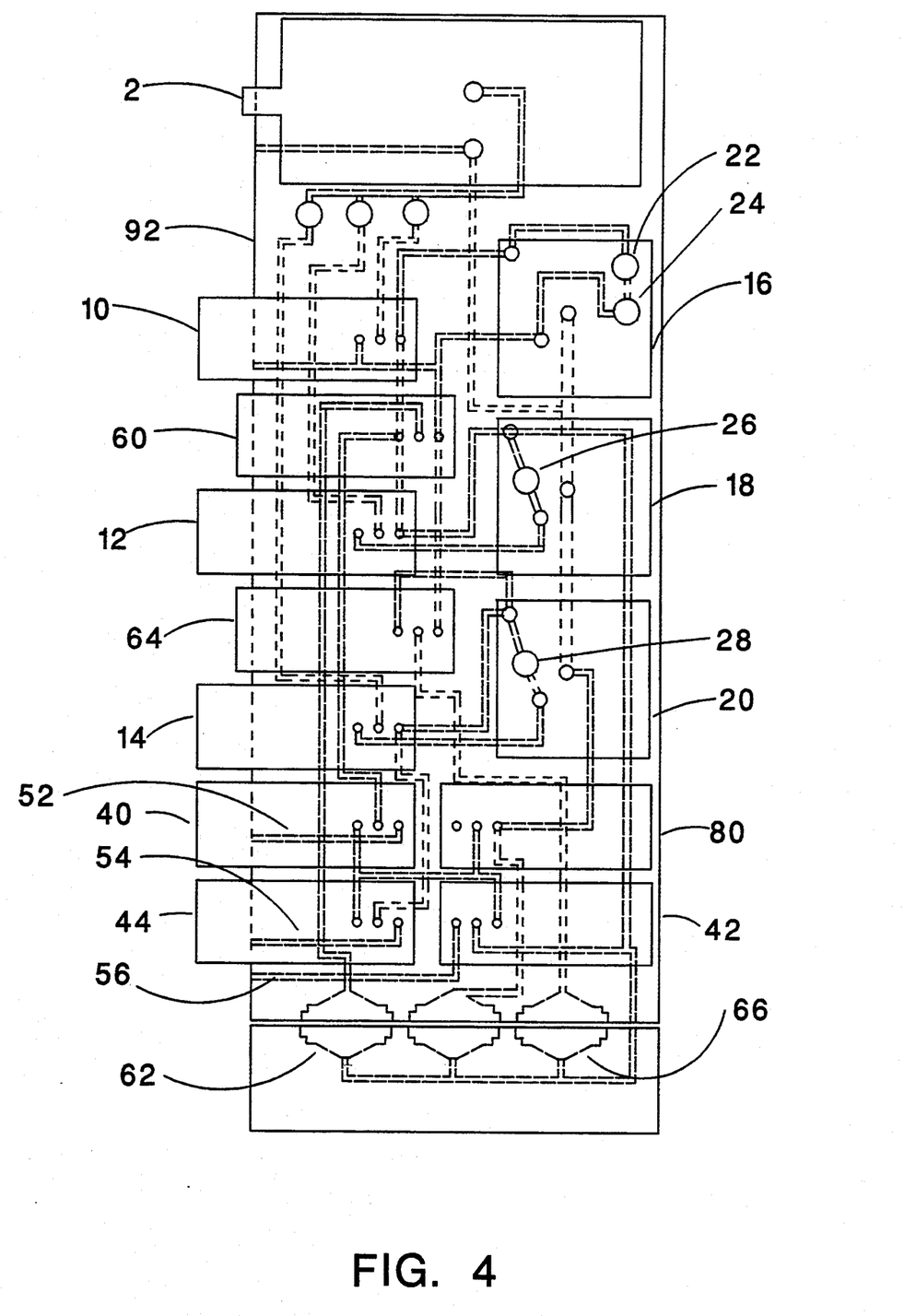
FIG. 4 is an elevation view of the pneumatic integrated circuit.

Referring to FIGS. 3 and 4, a presently preferred embodiment of the invention is presented. Pneumatic integrated circuit 90 comprises a plurality of the elements of the invention mounted on and within manifold 92. For the purposes of this disclosure, the term "manifold" means a component having chamber with a plurality of outlets through which a gas is distributed. Mounted on and within manifold 92 is source of compressed gas 2; first, second and third bubbler circuits 52, 54, and 56 connected to source of compressed gas 2; and means for controlling bubble release rate, comprising first adjustable spring-biased comparitor 16 and fourth and fifth orifices 22 and 24, second adjustable spring-biased comparitor 18 and sixth orifice 26, third adjustable spring-biased comparitor 20 and seventh orifice 28. One means for controlling bubble rate is associated with each bubbler circuit. Two means for sensing differential pressure, differential pressure sensors 62 and 66, are connected to the bubbler circuits. Differential pressure sensors 62 and 66 each have a pressure side and a reference side, and produce electrical signals proportional to the difference between the pressures applied to the pressure side and the reference side when excited with electrical power.

First solenoid valve 10, second solenoid valve 12, and third solenoid valve 14 provide means for providing high rate air purging to bubbler circuits 52, 54, and 56, respectively. Fourth solenoid valve 40, fifth solenoid valve 42, sixth solenoid valve 44, seventh solenoid valve 60, eighth solenoid valve 64, and ninth solenoid valve 80 provide means for simultaneously applying a single pressure to the pressure side and the reference side of said means for sensing differential pressure to produce a zero pressure signal. Fourth solenoid valve 40, fifth solenoid valve 42, sixth solenoid valve 44, seventh solenoid valve 60, eighth solenoid valve 64, ninth solenoid valve 80, and compressor 2 provide means for generating a known pressure that is different from atmospheric pressure, and means for simultaneously imposing said known pressure across said means for sensing differential pressure to produce a known pressure signal.

In the embodiment shown in FIGS. 3 and 4, manifold 92 is comprised of first layer 210, second layer 212 and third layer 214. The portions of first, second, and third bubbler circuits 52, 54, and 56 within manifold 92 are formed, in part, by machining channels in at least second layer 212 and third layer 214 and by drilling holes in at least first layer 210 and second layer 212. In this embodiment, the layer are held together and pneumatic separation of the channels is ensured by a layer of cement between each pair of layers. Maintenance of manifold 92 is facilitated by using as the cement Sashco Lexel, which cement can be removed by soaking manifold in kerosene, thereby allowing manifold 92 to be disassembled.

In other embodiments, the portions of first, second and third bubbler circuits 52, 54, and 56 within manifold 92 are formed, in part by providing a first compressible gasket (not shown) between first layer 210 and second layer 212 and a second compressible gasket (not shown) between second layer 212 and third layer 214. Channels are formed in the first and second compressible gaskets by injection molding or other conventional methods. In this embodiment, the layers can be held together with removable bolts.

Figure 5:
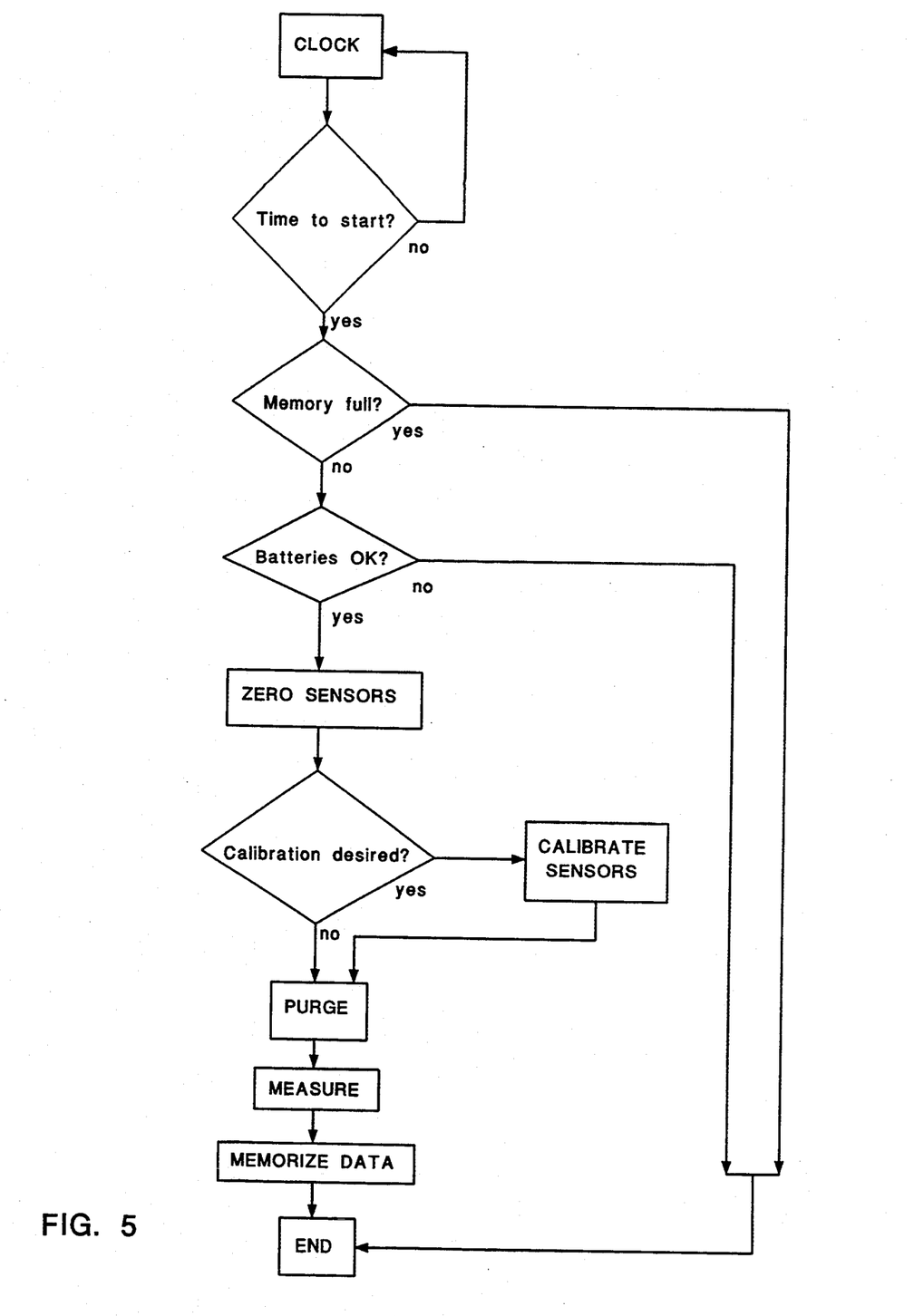
FIG. 5 is a flow chart for the datalogger/controller software program.

FIG. 5 is a flow chart for a preferred embodiment of a software program which is used to program the datalogger/controller. The flow chart illustrates the sequence of events that occur prior to each pressure measurement in the preferred mode of operation of apparatus 1.

Many variations of the invention will occur to those skilled in the art. For example, a variety of circuit designs could be used to accomplish the functions of the invention. All such variations within the scope of the claims are intended to be within the scope and spirit of the invention.

We claim:

1. A system for measuring the flow rate of a liquid comprising:
a primary element comprising a constriction in a closed conduit, said constriction having a modular limit and being configured so as
to cause at least one of the following to fill prior to said modular limit being reached:
said closed conduit, and
said constriction,
said constriction producing pressures in said liquid,
a source of compressed gas,
means for releasing a plurality of bubbles of said gas exposed to said pressures,
a plurality of bubbler circuits connected to said means for releasing a plurality of bubbles,
means for controlling bubble release rate,
at least one means for sensing differential pressure connected to said plurality of bubbler circuits, said means for sensing having a pressure side and a reference side, and said means for sensing producing a plurality of signals when excited, said plurality of signals being characterized by an offset or zero and a gain,
means for simultaneously applying a single pressure to the pressure side and the reference side of said means for sensing differential pressure to produce a zero pressure signal,
means for resetting the zero of said means for sensing differential pressure by reference to at least said zero pressure signal,
means for generating a known pressure differential,
wherein said means for generating a known pressure differential is selected from the group consisting of:
means for generating a known head and a known head loss,
means for sensing pressures at a plurality of known elevations or depths in a liquid,
means for sensing pressures at known elevations or depths in liquids of known density,
means for generating a known gauge pressure that is referenced to atmospheric pressure, and
means for generating a gas pressure that is regulated above atmospheric pressure,
means for simultaneously imposing said known pressure differential across each said means for sensing differential pressure to produce a known pressure signal,
means for resetting the gain of said means for sensing differential pressure by reference to at least said known pressure signal, and
means for determining said flow rate by reference to said plurality of signals.

2. The system of claim 1 wherein said constriction comprises a flow tube for temporary installation in a sewer having an approximately circular cross section.

3. The system of claim 1 wherein said means for sensing differential pressure comprises a temperature-compensated pressure transducer.

4. The system of claim 1 wherein said constriction comprises:
a venturi metering member for disposition in said closed conduit in a manner as to accept a flowing material in a flow path therethrough and otherwise substantially block the conduit;
said venturi metering member formed having a constricting inlet section in the direction of flow, terminating within said member in a throat sections, said throat section defined as a passage having a top and bottom and continuing from said constricting inlet section,
said throat having a cross section smaller than said inlet section and being configured in said member with a distance between its top and bottom, such that in use the throat fills at about the same time as said inlet section fills upstream upon increasing flow in said closed conduit,
wherein said means for releasing bubbles permits sensing of the pressure in the region of said constricting inlet section and in said throat in less than full and in full closed conduit flow condition.

5. The system of claim 1 further comprising:
a tubular venturi metering member for disposition in said closed conduit in a manner as to accept the flowing material in a flow path therethrough and otherwise substantially block said conduit,
said tubular venturi metering member formed having a constricting inlet section in the direction of flow, terminating within said member in a throat section, said throat section defined as a passage having a top and bottom continuing from said constricting inlet section and extending substantially parallel to the longitudinal axis of the said member,
said throat being positioned relative to said constricting inlet section to have a distance between the top and bottom of the throat such that it fills at the same flow rate as said inlet section fills upstream upon increasing flow in said closed conduit,
wherein said means for releasing bubbles permits sensing of the pressure in said constricting inlet section and in said throat in less than full and in full closed conduit flow conditions.

6. The system of claim 1 further comprising:
a closed conduit in which a liquid is flowing generally parallel to the longitudinal axis of said closed conduit due to gravity,
at least two different cross sections transverse to said conduit's axis, said cross sections adapted relative to one another such that the cross sections fill with liquid simultaneously as the flow rate of liquid in said closed conduit increases,
wherein said means for releasing bubbles are located adjacent said cross sections.

7. The system of claim 1 further comprising: at least one throat section having a top and a bottom, said at least one throat section being so constricted between said top and said bottom as to cause simultaneous filling of said throat section and said closed conduit upstream of said throat as the flow rate through said throat increases, and means operatively associated therewith for determining flow rate in less than full and full flow through said closed conduit.

8. The system of claim 1 further comprising:

a flow restriction in said closed conduit having a top and a bottom said restrocton being so constricted between said top and said bottom that said restriction fills on increasing volumetric flow rate at substantially the same volumetric flow rate as said closed conduit adjacent said restriction fills, wherein said means for releasing bubbles allow sensing the static pressure in less than full and full flow through said closed conduit.

9. A system for measuring the flow rate of a liquid comprising:

a primary element comprising a constriction in a closed conduit, said constriction having a modular limit and being configured so as to accomplish both of the following: to cause the constriction to fill with the liquid at substantially the same flow rate as the closed conduit upstream from said constriction, as the flow rate increases, and to cause at least one of the following to fill prior to said modular limit being reached;

said closed conduit, and said constriction, said constriction producing pressures in said liquid, a source of compressed gas, means for releasing a plurality of bubbles of said gas exposed to said pressures, a plurality of bubbler circuits connected to said means for releasing a plurality of bubbles, means for controlling bubble release rate, at least one means for sensing differential pressure connected to said plurality of bubbler circuits, said means for sensing having a pressure side and a reference side, and said means for sensing producing a plurality of signals when excited, means for simultaneously applying a single pressure to the pressure side and the reference side of said means for sensing differential pressure to produce a zero pressure signal, means for resetting the zero of said means for sensing differential pressure by reference to at least said zero pressure signal, means for generating a known pressure differential wherein said means for generating a known pressure differential is selected from the group consisting of:

means for generating a known head and a known head loss, means for sensing pressures at a plurality of known elevations or depths in a liquid, means for sensing pressures at known elevations or depths in liquids of known density, means for generating a known gauge pressure that is referenced to atmospheric pressure, means for generating a gas pressure that is regulated above atmospheric pressure, means for simultaneously imposing said known pressure differential across each said means for sensing differential pressure to produce a known pressure signal, means for resetting the gain of said means for sensing differential pressure by reference to at least said known pressure signal, and means for determining said flow rate by reference to said plurality of signals.

10. The system of claim 9 wherein said means for generating a known pressure comprises a differential pressure regulator.

11. The system of claim 9 wherein said means for generating a known pressure comprises a pressurized manometer.

12. The system of claim 9 wherein said means for generating a known pressure differential comprises:

an air compressor for producing a flow of air, an orifice constricting the flow of air, an adjustable differential pressure regulator for maintaining pressure drop across said orifice, and a manometer for measuring and indicating the magnitude of said pressure drop.

13. The system of claim 9 wherein said means for generating a known pressure differential comprises:

an air compressor for producing a flow of air, an orifice constricting the flow of air, an adjustable differential pressure regulator for maintaining a pressure drop across said orifice, a means for sensing the temperature of said flow of air, and means for determining said known pressure differential by reference to said means for sensing the temperature of said flow of air.

14. The system of claim 9 wherein said means for generating a known pressure differential comprises:

a compressor for pressuring a gas in a pneumatic circuit, an adjustable pressure regulator having an exhaust to ambient air pressure for maintaining a set pressure in said pneumatic circuit, means for sensing the temperature of said gas, and means for determining said known pressure differential by reference to said means for sensing the temperature of said gas.

15. The system of claim 9 further comprising:

a closed conduit in which said constriction is installed, a manhole on said closed conduit in which said means for determining said flow rate is installed, and means for determining when said manhole is surcharged.

16. The system of claim 9 further comprising:

a closed conduit in which said constriction is installed, a manhole on said closed conduit in which said means for determining said flow rate is installed, and means for determining when said closed conduit is full and said flow rate is essentially zero.

17. The system of claim 9 wherein said means for generating a known pressure is compensated for temperature variation by means of an algorithm, said algorithm being $$KDH = SH - C^*T$$

wherein KDH is a known differential head, SH is a differential head set across said means for generating a known pressure at a particular temperature, C is the temperature coefficient, and T is the temperature of said means for generating a known pressure.

18. The system of claim 9 wherein said means for generating a known pressure comprises a double-bubbler arrangement.

19. The system of claim 9 wherein said known pressure is variable so as to allow a high accuracy over a selected span of pressure measurement.

20. The system of claim 9 wherein said at least one means for sensing differential pressure has a span and a linear response to a plurality of different applied pressures and said known pressure is higher than said span so as to produce a greater accuracy of pressure measurement over said span.

21. The system of claim 9 wherein said means for recalibrating has an accuracy that is characterized by an error in pressure measurement expressed as a percent of full scale,
said error being less than an error achieved by a conventional temperature-compensated pressure transducer.

22. The system of claim 9 wherein said system comprises an integrated pneumatic circuit comprising a plurality of elements mounted on or within a manifold, said plurality of elements comprising:
said source of compressed gas,
said plurality of bubbler circuits connected to said source of compressed gas,
said means for releasing bubbles of said gas exposed to said pressures,
said means for controlling bubble release rate associated with said plurality of bubbler circuits,
said at least one means for sensing differential pressure connected to said plurality of bubbler circuits, said means for sensing having a pressure side and a reference side, and said means for sensing producing signals when excited,
said means for simultaneously applying a first pressure to the pressure side and the reference side of said means for sensing differential pressure to produce a zero pressure signal,
said means for zeroing said means for sensing differential pressure by reference to at least said zero pressure signal,
said means for generating a second known pressure that is different from atmospheric pressure,
said means for simultaneously imposing said known pressure to the pressure side and said first pressure to the reference side of said means for sensing differential pressure to produce a second pressure signal, and
said means for recalibrating said means for sensing differential pressure by reference to at least said second pressure signal.

23. The system of claim 9 comprising a datalogger/controller software program that causes said datalogger/controller to operate and store data.

24. The system of claim 9 comprising a datalogger/controller that stores data and a modem to transmit said data to a computer.

25. The system of claim 9 comprising a datalogger/controller that stores data and a packet radio station to transmit said data to a computer.

26. An apparatus for metering the flow of liquid which is flowing by gravity in an elongated pipe that is open to the atmosphere, comprising:
a tubular venturi metering device arranged in the pipe, which device has an open ended bore therethrough having an axis end-to-end thereof, said bore having an entrance section adjacent a first end thereof which converges toward the second end of the bore but terminates short of the axis of the bore so that the throat is formed in the bore which opens to said second end,
said device being arranged in the pipe to accept flow into said entrance from the pipe and otherwise to substantially block the pipe,
the cross-sectional area of the throat relative to that of the entrance section being configured so that the entrance will fill prior to the throat on rising water level before the modular limit is reached,
means for determining the head of liquid in said entrance section and in said throat.

27. An apparatus for metering the flow of liquid which is flowing by gravity in an elongated pipe that is open to the atmosphere, comprising:
a tubular venturi metering device arranged in the pipe, which device has an open ended bore therethrough having an axis end-to-end thereof, said bore having an entrance section adjacent a first end thereof which converges toward the second end of the bore but terminates short of the axis of the bore so that the throat is formed in the bore which opens to said second end,
said device being arranged in the pipe to accept flow into said entrance from the pipe and otherwise to substantially block the pipe,
the cross-sectional area of the throat relative to that of the entrance section being configured so that the throat will fill prior to the throat on rising water level before the modular limit is reached,
means for determining the head of liquid in said entrance section and in said throat.

* * * * *